US007226762B2

(12) United States Patent
Zelder et al.

(10) Patent No.: US 7,226,762 B2
(45) Date of Patent: Jun. 5, 2007

(54) GENE CODING FOR GLUCOSE-6-PHOSPHATE-DEHYDROGENASE PROTEINS

(75) Inventors: Oskar Zelder, Speyer (DE); Markus Pompejus, Waldsee (DE); Hartwig Schröder, Nussloch (DE); Burkhard Kröger, Limburgerhof (DE); Corinna Klopprogge, Ludwigshafen (DE); Gregor Haberhauer, Limburgerhof (DE)

(73) Assignee: BASF Aktiengesellschaft (DE)

( * ) Notice: Subject to any disclaimer, the term of this patent is extended or adjusted under 35 U.S.C. 154(b) by 31 days.

(21) Appl. No.: 10/495,291

(22) PCT Filed: Nov. 11, 2002

(86) PCT No.: PCT/EP02/12556

§ 371 (c)(1),
(2), (4) Date: May 11, 2004

(87) PCT Pub. No.: WO03/042389

PCT Pub. Date: May 22, 2003

(65) Prior Publication Data

US 2005/0014235 A1 Jan. 20, 2005

(30) Foreign Application Priority Data

Nov. 13, 2001 (DE) ................ 101 55 505

(51) Int. Cl.
C12P 13/04 (2006.01)
C12P 13/08 (2006.01)
C12N 9/02 (2006.01)
C12N 1/20 (2006.01)
C07H 21/02 (2006.01)

(52) U.S. Cl. ............ 435/106; 435/115; 435/189; 435/320.1; 435/252.3; 435/348; 435/325; 435/254.1; 536/23.1

(58) Field of Classification Search ............ 435/189, 435/320.1, 252.3, 348, 325, 254.1, 419, 115, 435/106; 536/23.1
See application file for complete search history.

(56) References Cited

FOREIGN PATENT DOCUMENTS

| WO | WO 01/00844 A2 | 1/2001 |
|---|---|---|
| WO | WO 01/04322 A1 | 1/2001 |
| WO | 1108790 A2 | 6/2001 |
| WO | WO 01/70995 A1 | 9/2001 |
| WO | WO 01/98472 A1 | 12/2001 |
| WO | WO 2005/075631 A1 * | 8/2005 |

OTHER PUBLICATIONS

Kalinowski J. et al. The complete *Corynebacterium glutamicum* ATCC13032 genome sequence and its impact on the production of L-aspartate-derived amino acids and vitamins, J. Biotechnol. 2003, 104, 5-25.*
Moritz et al. "Kinetic properties of the glucose-6-phosphate and 6-phosphogluconate dehydrogenases from *Corynebacterium glutamicum* and their application for predicting pentose phosphate pathway flux *in vivo.*" *Eur J Biochem.* Jun. 2000;267(12):3442-52.
Bathe, Brigitte et al, "A physical and genetic map of the *Corynebacterium glutamicum* ATCC 13032 chromosome," *Mol. Gen. Genet.*, vol. 252(3):255-265 (1996).
Cole, S.T. et al, "Deciphering the biology of *Mycobacterium tuberculosis* from the complete genome sequence," *Nature*, vol. 393(6685):537-544 (1998).
Database EMBL: Sequence (Online) Accession No. 006814. "6-phosphogluconolactolase (6PGL) of *Mycobacterium tuberculosis,*" Nov. 1, 1997.
Eikmanns, Bernhard J. et al, "The phosphoenolpyruvate carboxylase gene of *Corynebacterium glutamicum*: Molecular cloning, nucleotide sequence, and expression," *Mol. Gen. Genet.*, vol. 218:330-339 (1989).
Peters-Wendisch, Petra G. et al, "Pyruvate carboxylase from *Corynbacterium glutamicum*: characterization, expression and inactivation of the *pyc* gene," *Microbiology*, vol. 144:915-927 (1998).

* cited by examiner

*Primary Examiner*—Tekchand Saidha
*Assistant Examiner*—Malgorzata A. Walicka
(74) *Attorney, Agent, or Firm*—Lahive & Cockfield, LLP; Elizabeth A. Hanley; Maria Laccotripe Zacharakis

(57) ABSTRACT

The present invention relates to isolated nucleic acid molecules encoding mutants of glucose-6-phosphate dehydrogenase, and vectors and hosts cells including such nucleic acid molecules. These nucleic acid molecules are involved in the biosynthesis of a fine chemical, e.g., an amino acid such as lysine. The present invention also relates to methods of producing and modulating the production of fine chemicals, e.g., lysine, by culturing recombinant microorganisms containing these nucleic acid molecules under conditions such that the fine chemical is produced.

14 Claims, No Drawings

SEQUENCE LISTING

<160> NUMBER OF SEQ ID NOS: 2

<210> SEQ ID NO 1
<211> LENGTH: 1672
<212> TYPE: DNA
<213> ORGANISM: Corynebacterium glutamicum
<220> FEATURE:
<221> NAME/KEY: 5 UTR
<222> LOCATION: (1)..(100)
<220> FEATURE:
<221> NAME/KEY: CDS
<222> LOCATION: (101)..(1645)
<220> FEATURE:
<221> NAME/KEY: 3 UTR
<222> LOCATION: (1646)..(1672)

<400> SEQUENCE: 1

```
agcacgctgc atcagtaacg gcgacatgaa atcgaattag ttcgatctta tgtggccgtt        60
acacatcttt cattaaagaa aggatcgtga cactaccatc gtg agc aca aac acg        115
                                            Val Ser Thr Asn Thr
                                             1               5 acc ccc tcc agc tgg aca aac cca ctg cgc gac ccg cag gat aaa cga        163
Thr Pro Ser Ser Trp Thr Asn Pro Leu Arg Asp Pro Gln Asp Lys Arg
            10                  15                  20 ctc ccc cgc atc gct ggc cct tcc ggc atg gtg atc ttc ggt gtc act        211
Leu Pro Arg Ile Ala Gly Pro Ser Gly Met Val Ile Phe Gly Val Thr
        25                  30                  35 ggc gac ttg gct cga aag aag ctg ctc ccc gcc att tat gat cta gca        259
Gly Asp Leu Ala Arg Lys Lys Leu Leu Pro Ala Ile Tyr Asp Leu Ala
    40                  45                  50 aac cgc gga ttg ctg ccc cca gga ttc tcg ttg gta ggt tac ggc cgc        307
Asn Arg Gly Leu Leu Pro Pro Gly Phe Ser Leu Val Gly Tyr Gly Arg
55                  60                  65 cgc gaa tgg tcc aaa gaa gac ttt gaa aaa tac gta cgc gat gcc gca        355
Arg Glu Trp Ser Lys Glu Asp Phe Glu Lys Tyr Val Arg Asp Ala Ala
 70                  75                  80                  85 agt gct ggt gct cgt acg gaa ttc cgt gaa aat gtt tgg gag cgc ctc        403
Ser Ala Gly Ala Arg Thr Glu Phe Arg Glu Asn Val Trp Glu Arg Leu
                90                  95                 100 gcc gag ggt atg gaa ttt gtt cgc ggc aac ttt gat gat gat gca gct        451
```

-continued

| | |
|---|---|
| Ala Glu Gly Met Glu Phe Val Arg Gly Asn Phe Asp Asp Ala Ala<br>               105                     110                  115 | |
| ttc gac aac ctc gct gca aca ctc aag cgc atc gac aaa acc cgc ggc<br>Phe Asp Asn Leu Ala Ala Thr Leu Lys Arg Ile Asp Lys Thr Arg Gly<br>            120                    125                    130 | 499 |
| acc gcc ggc aac tgg gct tac tac ctg tcc att cca cca gat tcc ttc<br>Thr Ala Gly Asn Trp Ala Tyr Tyr Leu Ser Ile Pro Pro Asp Ser Phe<br>        135                    140                    145 | 547 |
| aca gcg gtc tgc cac cag ctg gag cgt tcc ggc atg gct gaa tcc acc<br>Thr Ala Val Cys His Gln Leu Glu Arg Ser Gly Met Ala Glu Ser Thr<br>150                    155                    160                  165 | 595 |
| gaa gaa gca tgg cgc cgc gtg atc atc gag aag cct ttc ggc cac aac<br>Glu Glu Ala Trp Arg Arg Val Ile Ile Glu Lys Pro Phe Gly His Asn<br>            170                    175                  180 | 643 |
| ctc gaa tcc gca cac gag ctc aac cag ctg gtc aac gca gtc ttc cca<br>Leu Glu Ser Ala His Glu Leu Asn Gln Leu Val Asn Ala Val Phe Pro<br>        185                    190                    195 | 691 |
| gaa tct tct gtg ttc cgc atc gac cac tat ttg ggc aag gaa aca gtt<br>Glu Ser Ser Val Phe Arg Ile Asp His Tyr Leu Gly Lys Glu Thr Val<br>            200                    205                  210 | 739 |
| caa aac atc ctg gct ctg cgt ttt gct aac cag ctg ttt gag cca ctg<br>Gln Asn Ile Leu Ala Leu Arg Phe Ala Asn Gln Leu Phe Glu Pro Leu<br>        215                    220                    225 | 787 |
| tgg aac tcc aac tac gtt gac cac gtc cag atc acc atg gct gaa gat<br>Trp Asn Ser Asn Tyr Val Asp His Val Gln Ile Thr Met Ala Glu Asp<br>230                    235                    240                  245 | 835 |
| att ggc ttg ggt gga cgt gct ggt tac tac gac ggc atc ggc gca gcc<br>Ile Gly Leu Gly Gly Arg Ala Gly Tyr Tyr Asp Gly Ile Gly Ala Ala<br>            250                    255                  260 | 883 |
| cgc gac gtc atc cag aac cac ctg atc cag ctc ttg gct ctg gtt gcc<br>Arg Asp Val Ile Gln Asn His Leu Ile Gln Leu Leu Ala Leu Val Ala<br>        265                    270                  275 | 931 |
| atg gaa gaa cca att tct ttc gtg cca gcg cag ctg cag gca gaa aag<br>Met Glu Glu Pro Ile Ser Phe Val Pro Ala Gln Leu Gln Ala Glu Lys<br>            280                    285                  290 | 979 |
| atc aag gtg ctc tct gcg aca aag ccg tgc tac cca ttg gat aaa acc<br>Ile Lys Val Leu Ser Ala Thr Lys Pro Cys Tyr Pro Leu Asp Lys Thr<br>295                    300                    305 | 1027 |
| tcc gct cgt ggt cag tac gct gcc ggt tgg cag ggc tct gag tta gtc<br>Ser Ala Arg Gly Gln Tyr Ala Ala Gly Trp Gln Gly Ser Glu Leu Val<br>310                    315                    320                  325 | 1075 |
| aag gga ctt cgc gaa gaa gat ggc ttc aac cct gag tcc acc act gag<br>Lys Gly Leu Arg Glu Glu Asp Gly Phe Asn Pro Glu Ser Thr Thr Glu<br>            330                    335                  340 | 1123 |
| act ttt gcg gct tgt acc tta gag atc acg tct cgt cgc tgg gct ggt<br>Thr Phe Ala Ala Cys Thr Leu Glu Ile Thr Ser Arg Arg Trp Ala Gly<br>        345                    350                    355 | 1171 |
| gtg ccg ttc tac ctg cgc acc ggt aag cgt ctt ggt cgc cgt gtt act<br>Val Pro Phe Tyr Leu Arg Thr Gly Lys Arg Leu Gly Arg Arg Val Thr<br>            360                    365                  370 | 1219 |
| gag att gcc gtg gtg ttt aaa gac gca cca cac cag cct ttc gac ggc<br>Glu Ile Ala Val Val Phe Lys Asp Ala Pro His Gln Pro Phe Asp Gly<br>375                    380                    385 | 1267 |
| gac atg act gta tcc ctt ggc caa aac gcc atc gtg att cgc gtg cag<br>Asp Met Thr Val Ser Leu Gly Gln Asn Ala Ile Val Ile Arg Val Gln<br>390                    395                    400                  405 | 1315 |
| cct gat gaa ggt gtg ctc atc cgc ttc ggt tcc aag gtt cca ggt tct<br>Pro Asp Glu Gly Val Leu Ile Arg Phe Gly Ser Lys Val Pro Gly Ser<br>            410                    415                  420 | 1363 |

```
gcc atg gaa gtc cgt gac gtc aac atg gac ttc tcc tac tca gaa tcc    1411
Ala Met Glu Val Arg Asp Val Asn Met Asp Phe Ser Tyr Ser Glu Ser
        425                 430                 435 ttc act gaa gaa tca cct gaa gca tac gag cgc ctc att ttg gat gcg    1459
Phe Thr Glu Glu Ser Pro Glu Ala Tyr Glu Arg Leu Ile Leu Asp Ala
        440                 445                 450 ctg tta gat gaa tcc agc ctc ttc cct acc aac gag gaa gtg gaa ctg    1507
Leu Leu Asp Glu Ser Ser Leu Phe Pro Thr Asn Glu Glu Val Glu Leu
    455                 460                 465 agc tgg aag att ctg gat cca att ctt gaa gca tgg gat gcc gat gga    1555
Ser Trp Lys Ile Leu Asp Pro Ile Leu Glu Ala Trp Asp Ala Asp Gly
470                 475                 480                 485 gaa cca gag gat tac cca gcg ggt acg tgg ggt cca aag agc gct gat    1603
Glu Pro Glu Asp Tyr Pro Ala Gly Thr Trp Gly Pro Lys Ser Ala Asp
                490                 495                 500 gaa atg ctt tcc cgc aac ggt cac acc tgg cgc agg cca taa            1645
Glu Met Leu Ser Arg Asn Gly His Thr Trp Arg Arg Pro
            505                 510                 515 tttaggggca aaaaatgatc tttgaac                                      1672

<210> SEQ ID NO 2
<211> LENGTH: 514
<212> TYPE: PRT
<213> ORGANISM: Corynebacterium glutamicum

<400> SEQUENCE: 2

Val Ser Thr Asn Thr Thr Pro Ser Ser Trp Thr Asn Pro Leu Arg Asp
  1               5                  10                  15

Pro Gln Asp Lys Arg Leu Pro Arg Ile Ala Gly Pro Ser Gly Met Val
                 20                  25                  30

Ile Phe Gly Val Thr Gly Asp Leu Ala Arg Lys Lys Leu Leu Pro Ala
             35                  40                  45

Ile Tyr Asp Leu Ala Asn Arg Gly Leu Leu Pro Pro Gly Phe Ser Leu
         50                  55                  60

Val Gly Tyr Gly Arg Arg Glu Trp Ser Lys Glu Asp Phe Glu Lys Tyr
 65                  70                  75                  80

Val Arg Asp Ala Ala Ser Ala Gly Ala Arg Thr Glu Phe Arg Glu Asn
                 85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125

Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240
```

-continued

```
Thr Met Ala Glu Asp Ile Gly Leu Gly Gly Arg Ala Gly Tyr Tyr Asp
            245             250             255
Gly Ile Gly Ala Ala Arg Asp Val Ile Gln Asn His Leu Ile Gln Leu
            260             265             270
Leu Ala Leu Val Ala Met Glu Glu Pro Ile Ser Phe Val Pro Ala Gln
            275             280             285
Leu Gln Ala Glu Lys Ile Lys Val Leu Ser Ala Thr Lys Pro Cys Tyr
            290             295             300
Pro Leu Asp Lys Thr Ser Ala Arg Gly Gln Tyr Ala Ala Gly Trp Gln
305             310             315             320
Gly Ser Glu Leu Val Lys Gly Leu Arg Glu Glu Asp Gly Phe Asn Pro
            325             330             335
Glu Ser Thr Thr Glu Thr Phe Ala Ala Cys Thr Leu Glu Ile Thr Ser
            340             345             350
Arg Arg Trp Ala Gly Val Pro Phe Tyr Leu Arg Thr Gly Lys Arg Leu
            355             360             365
Gly Arg Arg Val Thr Glu Ile Ala Val Val Phe Lys Asp Ala Pro His
370             375             380
Gln Pro Phe Asp Gly Asp Met Thr Val Ser Leu Gly Gln Asn Ala Ile
385             390             395             400
Val Ile Arg Val Gln Pro Asp Glu Gly Val Leu Ile Arg Phe Gly Ser
            405             410             415
Lys Val Pro Gly Ser Ala Met Glu Val Arg Asp Val Asn Met Asp Phe
            420             425             430
Ser Tyr Ser Glu Ser Phe Thr Glu Glu Ser Pro Glu Ala Tyr Glu Arg
            435             440             445
Leu Ile Leu Asp Ala Leu Leu Asp Glu Ser Ser Leu Phe Pro Thr Asn
450             455             460
Glu Glu Val Glu Leu Ser Trp Lys Ile Leu Asp Pro Ile Leu Glu Ala
465             470             475             480
Trp Asp Ala Asp Gly Glu Pro Glu Asp Tyr Pro Ala Gly Thr Trp Gly
            485             490             495
Pro Lys Ser Ala Asp Glu Met Leu Ser Arg Asn Gly His Thr Trp Arg
            500             505             510
Arg Pro
```

GENE CODING FOR GLUCOSE-6-PHOSPHATE-DEHYDROGENASE PROTEINS

RELATED APPLICATIONS

This application is a national stage application of International Application No. PCT/EP02/12556, filed on Nov. 11, 2002, which claims priority to German Application No. 10155505.9, filed Nov. 13, 2001. The entire contents of each of these applications are expressly incorporated herein by this reference.

BACKGROUND OF THE INVENTION

Particular products and byproducts of naturally occurring metabolic processes in cells are used in many branches of industry, including the food industry, the animal feed industry, the cosmetics industry and the pharmaceutical industry. These molecules which are collectively referred to as "fine chemicals" comprise organic acids, both proteinogenic and nonproteinogenic amino acids, nucleotides and nucleosides, lipids and fatty acids, diols, carbohydrates, aromatic compounds, vitamins, cofactors and enzymes. They are best produced by means of cultivating, on a large scale, bacteria which have been developed to produce and secrete large amounts of the molecule desired in each particular case. An organism which is particularly suitable for this purpose is *Corynebacterium glutamicum*, a Gram-positive nonpathogenic bacterium. Using strain selection, a number of mutant strains have been developed which produce various desirable compounds. The selection of strains which are improved with respect to the production of a particular molecule is, however, a time-consuming and difficult process.

BRIEF DESCRIPTION OF THE INVENTION

The present invention provides novel nucleic acid molecules which can be used for identifying or classifying *Corynebacterium glutamicum* or related bacterial species. *C. glutamicum* is a Gram-positive, aerobic bacterium which is widely used in industry for the large-scale production of a number of fine chemicals and also for the degradation of hydrocarbons (for example in the case of crude oil spills) and for the oxidation of terpenoids. The nucleic acid molecules may therefore be used for identifying microorganisms which can be used for producing fine chemicals, for example by fermentation processes. Although *C. glutamicum* itself is nonpathogenic, it is, however, related to other *Corynebacterium species* such as *Corynebacterium diphteriae* (the diphtheria pathogen), which are major pathogens in humans. The ability to identify the presence of *Corynebacterium* species may therefore also be of significant clinical importance, for example in diagnostic applications. Moreover, said nucleic acid molecules may serve as reference points for mapping the *C. glutamicum* genome or genomes of related organisms.

These novel nucleic acid molecules encode proteins which are referred to as glucose-6-phosphate-dehydrogenase proteins.

Glucose-6-phosphate-dehydrogenase genes from *Corynebacteria* are described, for example, in EP 1108790A2. However, the genes described therein code for polypeptide sequences which are shorter than those described herein according to the invention. The N terminus of the glucose-6-phosphate-dehydrogenase described in EP 1108790A2 is truncated by 30 amino acids compared with the polypeptide sequence claimed herein.

Moritz et al. (Eur. J. Biochemistry 267, 3442–3452, 2000) describe the isolation of a glucose-6-phosphate-dehydrogenase from *Corynebacterium glutamicum*. The N-terminal protein sequencing described therein results in a polypeptide which starts with a serine and differs from the protein of the invention.

The invention relates to novel genes for glucose-6-phosphate-dehydrogenase, which start with the amino acid at position 1 or 2, i.e. Val or Ser and which encode at position 243 a proteinogenic amino acid which is not Ala (numbering based on SEQ ID NO: 2).

Particular preference is given to novel genes for glucose-6-phosphate-dehydrogenase, which start with the amino acid at position 1 and encode Thr at position 243 (numbering based on SEQ ID NO: 2).

The nucleic acid molecules of the invention can be used for genetic manipulation of an organism in order to make it a better and more efficient producer of one or more fine chemicals. The molecules of the invention can be modified so as to improve the yield, production and/or efficiency of production of one or more fine chemicals.

Furthermore, the molecules of the invention may be involved in one or more intracellular signal transduction pathways which influence the yields and/or the rate of production of one or more fine chemicals from *C. glutamicum*. Proteins which are required, for example, for importing one or more sugars from the extracellular medium (e.g. Hpr, enzyme I or a component of the enzyme II complex) are, if a sufficient amount of sugar is present in the cell, frequently posttranslationally modified so that they are no longer able to import said sugar. Although the amount of sugar at which the transport system is switched off is sufficient for maintaining normal cellular functions, it limits overproduction of the fine chemical of interest. It is therefore recommended to modify the proteins of the invention so that they no longer respond to such a negative regulation. As a result, it is possible to attain higher intracellular concentrations of one or more sugars and, by extension, a more efficient production or higher yields of one or more fine chemicals from organisms which contain said mutant proteins.

Appendix A defines hereinbelow the nucleic acid sequences of the sequence listing together with the sequence modifications at the relevant position, described in Table 1.

Appendix B defines hereinbelow the polypeptide sequences of the sequence listing together with the sequence modifications at the relevant position, described in Table 1.

In a further embodiment, the isolated nucleic acid molecule is at least 15 nucleotides in length and hybridizes under stringent conditions to a nucleic acid molecule which comprises a nucleotide sequence of Appendix A. The isolated nucleic acid molecule preferably corresponds to a naturally occurring nucleic acid molecule. The isolated nucleic acid more preferably encodes a naturally occurring *C. glutamicum* G6PD protein or a biologically active section thereof.

A further aspect of the invention relates to vectors, for example recombinant expression vectors, which contain the nucleic acid molecules of the invention and to host cells into which said vectors have been introduced. In one embodiment, a G6PD protein is prepared by using a host cell which is cultivated in a suitable medium. The G6PD protein may then be isolated from the medium or the host cell.

A further aspect of the invention relates to a genetically modified microorganism into which a G6PD gene has been introduced or in which a G6PD gene has been modified. In one embodiment, the genome of said microorganism has been modified by introducing at least one inventive nucleic acid molecule which encodes the mutated G6PD sequence as transgene. In another embodiment, an endogenous G6PD gene in the genome of said microorganism has been modified, for example, functionally disrupted, by homologous recombination with a modified G6PD gene. In a preferred embodiment, the microorganism belongs to the genus *Corynebacterium* or *Brevibacterium*, with *Corynebacterium glutamicum* being particularly preferred. In a preferred embodiment, the microorganism is also used for preparing a compound of interest, such as an amino acid, particularly preferably lysine.

Another preferred embodiment are host cells having more than one of the nucleic acid molecules described in Appendix A. Such host cells can be prepared in various ways known to the skilled worker. They may be transfected, for example, by vectors carrying several of the nucleic acid molecules of the invention. However, it is also possible to use a vector for introducing in each case one nucleic acid molecule of the invention into the host cell and therefore to use a plurality of vectors either simultaneously or sequentially. Thus it is possible to construct host cells which carry numerous, up to several hundred, nucleic acid sequences of the invention. Such an accumulation can often produce superadditive effects on the host cell with respect to fine-chemical productivity.

A further aspect of the invention relates to an isolated G6PD protein or a section thereof, for example a biologically active section. In a preferred embodiment, the isolated G6PD protein or its section may be involved in importing energy-rich carbon molecules (e.g. glucose, fructose or sucrose) into *C. glutamicum* and, moreover, in one or more intracellular signal transduction pathways of *C. glutamicum*. In another preferred embodiment, the isolated G6PD protein or a section thereof is sufficiently homologous to an amino acid sequence of Appendix B so that the protein or its section is still capable of taking part in importing energy-rich carbon molecules (e.g. glucose, fructose or sucrose) into *C. glutamicum* and/or in one or more intracellular signal transduction pathways of *C. glutamicum*.

Moreover, the invention relates to an isolated glu-6-phosphate-dehydrogenase protein preparation. In preferred embodiments, the glu-6-phosphate-dehydrogenase (G6PD) protein comprises an amino acid sequence of Appendix B. In a further preferred embodiment, the invention relates to an isolated full-length protein which is essentially homologous to a complete amino acid sequence of Appendix B (which is encoded by an open reading frame in Appendix A).

A further aspect of the invention relates to a method for preparing a fine chemical. The method provides for the cultivation of a cell containing a vector which causes expression of a nucleic acid molecule of the invention so that a fine chemical is produced. In a preferred embodiment, this method moreover comprises the step of obtaining a cell containing such a vector, said cell being transfected with a vector which causes expression of a nucleic acid. In a further preferred embodiment, said method moreover comprises the step in which the fine chemical is obtained from the culture. In a preferred embodiment, the cell belongs to the genus *Corynebacterium* or *Brevibacterium*.

I. Fine Chemicals

The term "fine chemicals" is known in the art and includes molecules which are produced by an organism and are used in various branches of industry such as, for example, but not restricted to, the pharmaceutical industry, the agricultural industry and the cosmetics industry. These compounds comprise organic acids such as tartaric acid, itaconic acid and diaminopimelic acid, both proteinogenic and nonproteinogenic amino acids, purine and pyrimidine bases, nucleosides and nucleotides (as described, for example, in Kuninaka, A. (1996) Nucleotides and related compounds, pp. 561–612, in Biotechnology Vol. 6, Rehm et al., Editors VCH: Weinheim and the references therein), lipids, saturated and unsaturated fatty acids (e.g. arachidonic acid), diols (e.g. propanediol and butanediol), carbohydrates (e.g. hyaluronic acid and trehalose), aromatic compounds (e.g. aromatic amines, vanilline and indigo), vitamins and cofactors (as described in Ullmann's Encyclopedia of Industrial Chemistry, Vol. A27. "Vitamines", pp. 443–613 (1196) VCH: Weinheim and the references therein; and Ong, A. S., Niki, E. and Packer, L. (1995) "Nutrition, Lipids, Health and Disease" Proceedings of the UNESCO/Confederation of Scientific and Technological Associations in Malaysia and the Society for Free Radical Research—Asia, held Sept. 1–3, 1994 in Penang, Malaysia, AOCS Press (1995)), enzymes and all other chemicals described by Gutcho (1983) in Chemicals by Fermentation, Noyes Data Corporation, ISBN: 0818805086 and the references indicated therein. The metabolism and the uses of particular fine chemicals are further illustrated below.

A. Amino Acid Metabolism and Uses

Amino acids comprise the fundamental structural units of all proteins and are thus essential for normal functions of the cell. The term "amino acid" is known in the art. Proteinogenic amino acids, of which there are 20 types, serve as structural units for proteins, in which they are linked together by peptide bonds, whereas the nonproteinogenic amino acids (hundreds of which are known) usually do not occur in proteins (see Ullmann's Encyclopedia of Industrial Chemistry, Vol. A2, pp. 57–97 VCH: Weinheim (1985)). Amino acids can exist in the D or L configuration, although L-amino acids are usually the only type found in naturally occurring proteins. Biosynthetic and degradation pathways of each of the 20 proteinogenic amino acids are well characterized both in prokaryotic and eukaryotic cells (see, for example, Stryer, L. Biochemistry, $3^{rd}$ edition, pp. 578–590 (1988)). The "essential" amino acids (histidine, isoleucine, leucine, lysine, methionine, phenylalanine, threonine, tryptophan and valine), so called because, owing to the complexity of their biosyntheses, they must be taken in with the diet, are converted by simple biosynthetic pathways into the other 11 "nonessential" amino acids (alanine, arginine, asparagine, aspartate, cysteine, glutamate, glutamine, glycine, proline, serine and tyrosine). Higher animals are able to synthesize some of these amino acids but the essential amino acids must be taken in with the food in order that normal protein synthesis takes place.

Apart from their function in protein biosynthesis, these amino acids are interesting chemicals as such, and it has been found that many have various applications in the human food, animal feed, chemicals, cosmetics, agricultural and pharmaceutical industries. Lysine is an important amino acid not only for human nutrition but also for monogastric livestock such as poultry and pigs. Glutamate is most frequently used as flavor additive (monosodium glutamate, MSG) and elsewhere in the food industry, as are aspartate, phenylalanine, glycine and cysteine. Glycine, L-methionine and tryptophan are all used in the pharmaceutical industry. Glutamine, valine, leucine, isoleucine, histidine, arginine, proline, serine and alanine are used in the pharmaceutical industry and the cosmetics industry. Threonine, tryptophan and D/L-methionine are widely used animal feed additives (Leuchtenberger, W. (1996) Amino acids—technical production and use, pp. 466–502 in Rehm et al., (editors) Biotechnology Vol. 6, Chapter 14a, VCH: Weinheim). It has been found that these amino acids are additionally suitable as precursors for synthesizing synthetic amino acids and proteins, such as N-acetylcysteine, S-carboxymethyl-L-cysteine, (S)-5-hydroxytryptophan and other substances described in Ullmann's Encyclopedia of Industrial Chemistry, Vol. A2, pp. 57–97, VCH, Weinheim, 1985.

The biosynthesis of these natural amino acids in organisms able to produce them, for example bacteria, has been well characterized (for a review of bacterial amino acid biosynthesis and its regulation, see Umbarger, H. E. (1978) Ann. Rev. Biochem. 47: 533–606). Glutamate is synthesized by reductive amination of α-ketoglutarate, an intermediate product in the citric acid cycle. Glutamine, proline and arginine are each generated successively from glutamate. The biosynthesis of serine takes place in a three-step process and starts with 3-phosphoglycerate (an intermediate product of glycolysis), and affords this amino acid after oxidation, transamination and hydrolysis steps. Cysteine and glycine are each produced from serine, specifically the former by condensation of homocysteine with serine, and the latter by transfer of the side-chain β-carbon atom to tetrahydrofolate in a reaction catalyzed by serine transhydroxy-methylase. Phenylalanine and tyrosine are synthesized from the precursors of the glycolysis and pentose phosphate pathway, and erythrose 4-phosphate and phosphoenolpyruvate in a 9-step biosynthetic pathway which diverges only in the last two steps after the synthesis of prephenate. Tryptophan is likewise produced from these two starting molecules but it is synthesized by an 11-step pathway. Tyrosine can also be prepared from phenylalanine in a reaction catalyzed by phenylalanine hydroxylase. Alanine, valine and leucine are each biosynthetic products derived from pyruvate, the final product of glycolysis. Aspartate is formed from oxalacetate, an intermediate product of the citrate cycle. Asparagine, methionine, threonine and lysine are each produced by the conversion of aspartate. Isoleucine is formed from threonine. Histidine is formed from 5-phosphoribosyl 1-pyrophosphate, an activated sugar, in a complex 9-step pathway.

Amounts of amino acids exceeding those required for protein biosynthesis by the cell cannot be stored and are instead broken down so that intermediate products are provided for the principal metabolic pathways in the cell (for a review, see Stryer, L., Biochemistry, $3^{rd}$ edition, Chapter 21 "Amino Acid Degradation and the Urea Cycle"; pp. 495–516 (1988)). Although the cell is able to convert unwanted amino acids into the useful intermediate products of metabolism, production of amino acids is costly in terms of energy, the precursor molecules and the enzymes necessary for their synthesis. It is therefore not surprising that amino acid biosynthesis is regulated by feedback inhibition, whereby the presence of a particular amino acid slows down or completely stops its own production (for a review of the feedback mechanism in amino acid biosynthetic pathways, see Stryer, L., Biochemistry, $3^{rd}$ edition, Chapter 24, "Biosynthesis of Amino Acids and Heme", pp. 575–600 (1988)). The output of a particular amino acid is therefore restricted by the amount of this amino acid in the cell.

B. Vitamins, Cofactors and Nutraceutical Metabolism, and Uses

Vitamins, cofactors and nutraceuticals comprise another group of molecules. Higher animals have lost the ability to synthesize them and therefore have to take them in, although they are easily synthesized by other organisms such as bacteria. These molecules are either bioactive molecules per se or precursors of bioactive substances which serve as electron carriers or intermediate products in a number of metabolic pathways. Besides their nutritional value, these compounds also have a significant industrial value as colorants, antioxidants and catalysts or other processing auxiliaries. (For a review of the structure, activity and industrial applications of these compounds, see, for example, Ullmann's Encyclopedia of Industrial Chemistry, "Vitamins", Vol. A27, pp. 443–613, VCH: Weinheim, 1996). The term "vitamin" is known in the art and comprises nutrients which are required for normal functional of an organism but cannot be synthesized by this organism itself. The group of vitamins may include cofactors and nutraceutical compounds. The term "cofactor" comprises nonproteinaceous compounds necessary for the appearance of a normal enzymic activity. These compounds may be organic or inorganic; the cofactor molecules of the invention are preferably organic. The term "nutraceutical" comprises food additives which are health-promoting in plants and animals, especially humans. Examples of such molecules are vitamins, antioxidants and likewise certain lipids (e.g. polyunsaturated fatty acids).

The biosynthesis of these molecules in organisms able to produce them, such as bacteria, has been comprehensively characterized (Ullmann's Encyclopedia of Industrial Chemistry, "Vitamins", Vol. A27, pp. 443–613, VCH: Weinheim, 1996, Michal, G. (1999) Biochemical Pathways: An Atlas of Biochemistry and Molecular Biology, John Wiley & Sons; Ong, A. S., Niki, E. and Packer, L. (1995) "Nutrition, Lipids, Health and Disease" Proceedings of the UNESCO/Confederation of Scientific and Technological Associations in Malaysia and the Society for free Radical Research—Asia, held on Sept. 1–3, 1994, in Penang, Malaysia, AOCS Press, Champaign, Ill. X, 374 S).

Thiamine (vitamin $B_1$) is formed by chemical coupling of pyrimidine and thiazole units. Riboflavin (vitamin $B_2$) is synthesized from guanosine 5'-triphosphate (GTP) and ribose 5'-phosphate. Riboflavin in turn is employed for the synthesis of flavin mononucleotide (FMN) and flavin adenine dinucleotide (FAD). The family of compounds together referred to as "vitamin B6" (for example pyridoxine, pyridoxamine, pyridoxal 5' phosphate and the commercially used pyridoxine hydrochloride), are all derivatives of the common structural unit 5-hydroxy-6-methylpyridine.

Panthothenate (pantothenic acid, R-(+)-N-(2,4-dihydroxy-3,3-dimethyl-1-oxobutyl)-β-alanine) can be prepared either by chemical synthesis or by fermentation. The last steps in pantothenate biosynthesis consist of ATP-driven condensation of β-alanine and pantoic acid. The enzymes responsible for the biosynthetic steps for the conversion into pantoic acid and into β-alanine and for the condensation to pantothenic acid are known. The metabolically active form of pantothenate is coenzyme A whose biosynthesis takes place by 5 enzymatic steps. Pantothenate, pyridoxal 5' phosphate, cysteine and ATP are the precursors of coenzyme A. These enzymes catalyze not only the formation of pantothenate but also the production of (R)-pantoic acid, (R)-pantolactone, (R)-panthenol (provitamin $B_5$), pantetheine (and its derivatives) and coenzyme A.

The biosynthesis of biotin from the precursor molecule pimeloyl-CoA in microorganisms has been investigated in detail, and several of the genes involved have been identified. It has emerged that many of the corresponding proteins are involved in the Fe cluster synthesis and belong to the class of nifS proteins. Liponic acid is derived from octanonoic acid and serves as coenzyme in energy metabolism where it is a constituent of the pyruvate dehydrogenase complex and of the α-ketoglutarate dehydrogenase complex. Folates are a group of substances all derived from folic acid which in turn is derived from L-glutamic acid, p-aminobenzoic acid and 6-methylpterin. The biosynthesis of folic acid and its derivatives starting from the metabolic intermediate products of the biotransformation of guanosine 5'-triphosphate (GTP), L-glutamic acid and p-aminobenzoic acid has been investigated in detail in certain microorganisms.

Corrinoids (such as the cobalamines and, in particular, vitamin $B_{12}$) and the porphyrins belong to a group of chemicals distinguished by a tetrapyrrole ring system. The biosynthesis of vitamin $B_{12}$ is so complex that it has not yet been completely characterized, but many of the enzymes and substrates involved are now known. Nicotinic acid (nicotinate) and nicotinamide are pyridine derivatives which are also referred to as "niacin". Niacin is the precursor of the important coenzymes NAD (nicotinamide adenine dinucleotide) and NADP (nicotinamide adenine dinucleotide phosphate) and their reduced forms.

Production of these compounds on the industrial scale is mostly based on cell-free chemical syntheses, although some of these chemicals have likewise been produced by large-scale cultivation of microorganisms, such as riboflavin, vitamin $B_6$, pantothenate and biotin. Only vitamin $B_{12}$ is, because of the complexity of its synthesis, produced only by fermentation. In vitro processes require a considerable expenditure of materials and time and frequently high costs.

C. Purine, Pyrimidine, Nucleoside and Nucleotide Metabolism and Uses

Genes for purine and pyrimidine metabolism and their corresponding proteins are important aims for the therapy of oncoses and viral infections. The term "purine" or "pyrimidine" comprises nitrogen-containing bases which form part of nucleic acids, coenzymes and nucleotides. The term "nucleotide" encompasses the fundamental structural units of nucleic acid molecules, which comprise a nitrogen-containing base, a pentose sugar (the sugar is ribose in the case of RNA and the sugar is D-deoxyribose in the case of DNA) and phosphoric acid. The term "nucleoside" comprises molecules which serve as precursors of nucleotides but have, in contrast to the nucleotides, no phosphoric acid unit. It is possible to inhibit RNA and DNA synthesis by inhibiting the biosynthesis of these molecules or their mobilization to form nucleic acid molecules; targeted inhibition of this activity in cancerogenic cells allows the ability of tumor cells to divide and replicate to be inhibited.

There are also nucleotides which do not form nucleic acid molecules but serve as energy stores (i.e. AMP) or as coenzymes (i.e. FAD and NAD).

Several publications have described the use of these chemicals for these medical indications, the purine and/or pyrimidine metabolism being influenced (for example Christopherson, R. I. and Lyons, S. D. (1990) "Potent inhibitors of de novo pyrimidine and purine biosynthesis as chemotherapeutic agents", Med. Res. Reviews 10: 505–548). Investigations of enzymes involved in purine and pyrimidine metabolism have concentrated on the development of novel medicaments which can be used, for example, as immunosuppressants or antiproliferative agents (Smith, J. L. "Enzymes in Nucleotide Synthesis" Curr. Opin. Struct. Biol. 5 (1995) 752–757; Biochem. Soc. Transact. 23 (1995) 877–902). However, purine and pyrimidine bases, nucleosides and nucleotides also have other possible uses: as intermediate products in the biosynthesis of various fine chemicals (e.g. thiamine, S-adenosylmethionine, folates or riboflavin), as energy carriers for the cell (for example ATP or GTP) and for chemicals themselves, are ordinarily used as flavor enhancers (for example IMP or GMP) or for many medical applications (see, for example, Kuninaka, A., (1996) "Nucleotides and Related Compounds in Biotechnology" Vol. 6, Rehm et al., editors VCH: Weinheim, pp. 561–612). Enzymes involved in purine, pyrimidine, nucleoside or nucleotide metabolism are also increasingly serving as targets against which chemicals are being developed for crop protection, including fungicides, herbicides and insecticides.

The metabolism of these compounds in bacteria has been characterized (for reviews, see, for example, Zalkin, H. and Dixon, J. E. (1992) "De novo purine nucleotide biosynthesis" in Progress in Nucleic Acids Research and Molecular biology, Vol. 42, Academic Press, pp. 259–287; and Michal, G. (1999) "Nucleotides and Nucleosides"; Chapter 8 in : Biochemical Pathways: An Atlas of Biochemistry and Molecular Biology, Wiley, N.Y.). Purine metabolism, the object of intensive research, is essential for normal functioning of the cell. Disordered purine metabolism in higher animals may cause severe illnesses, for example gout. Purine nucleotides are synthesized from ribose 5-phosphate by a number of steps via the intermediate compound inosine 5'-phosphate (IMP), leading to the production of guanosine 5'-monophosphate (GMP) or adenosine 5'-monophosphate (AMP), from which the triphosphate forms used as nucleotides can easily be prepared. These compounds are also used as energy stores, so that breakdown thereof provides energy for many different biochemical processes in the cell. Pyrimidine biosynthesis takes place via formation of uridine 5'-mono-phosphate (UMP) from ribose 5-phosphate. UMP in turn is converted into cytidine 5'-triphosphate (CTP). The deoxy forms of all nucleotides are prepared in a one-step reduction reaction from the diphosphate ribose form of the nucleotide to give the diphosphate deoxyribose form of the nucleotide. After phosphorylation, these molecules can take part in DNA synthesis.

D. Trehalose Metabolism and Uses

Trehalose consists of two glucose molecules linked together by α,α-1,1 linkage. It is ordinarily used in the food industry as sweetener, as additive for dried or frozen foods and in beverages. However, it is also used in the pharmaceutical industry or in the cosmetics industry and biotechnology industry (see, for example, Nishimoto et al., (1998) U.S. Pat. No. 5,759,610; Singer, M. A. and Lindquist, S. Trends Biotech. 16 (1998) 460–467; Paiva, C. L. A. and Panek, A. D. Biotech Ann. Rev. 2 (1996) 293–314; and Shiosaka, M. J. Japan 172 (1997) 97–102). Trehalose is produced by enzymes of many microorganisms and is naturally released into the surrounding medium from which it can be isolated by methods known in the art.

II. Elements and Methods of the Invention

The present invention is based, at least partially, on the detection of new molecules which are referred to herein as G6PD nucleic-acid and G6PD-protein molecules and which are involved in taking up energy-rich carbon molecules (e.g. glucose, sucrose and fructose) into *C. glutamicum* and may also be involved in one or more intracellular signal transduction pathways in this microorganism. In one embodiment, the G6PD molecules import energy-rich carbon molecules into the cell in which the energy generated by their degradation is used for driving energetically less favored biochemical reactions. Their degradation products may be used as intermediates or precursors for a number of other metabolic pathways. In another embodiment, the G6PD molecules may take part in one or more intracellular signal transduction pathways, and the presence of a modified form of a G6PD molecule (e.g. a phosphorylated G6PD protein) may take part in a signal transduction cascade which regulates one or more cellular processes. In a preferred embodiment, the activity of the G6PD molecules of the invention affects the production of a fine chemical of interest by said organism. In a particularly preferred embodiment, the activity of the G6PD molecules of the invention is modulated so that the yield, production or efficiency of production of one or more fine chemicals from *C. glutamicum* is likewise modulated.

In another embodiment, the G6PD molecules of the invention are capable of modulating the production of a molecule of interest, such as a fine chemical, in a microorganism such as *C. glutamicum*. It is possible, with the aid of gene recombination techniques, to manipulate one or more G6PD proteins of the invention in such a way that their function is modulated. For example, a protein involved in the G6PD-mediated import of glucose may be modified for it to have optimal activity, and the G6PD system for importing glucose is thus able to transport larger amounts of glucose to the cell. Glucose molecules are used not only as energy source for energetically unfavorable biochemical reactions such as the biosynthesis of fine chemicals, but also as precursors and intermediates in a number of biosynthetic pathways of fine chemicals (for example, serine is synthesized from 3-phosphoglycerate). In any case, it is possible to increase the overall yield or the rate of production of any of these fine chemicals of interest, that is by increasing the energy available for said production to take place or by increasing the availability of the compounds required for said production to take place.

A suitable starting point for preparing the nucleic acid sequences of the invention is the genome of a *Corynebacterium glutamicum* strain which can be obtained from the American Type Culture Collection under the name ATCC 13032.

The nucleic acid sequences of the invention can be prepared from these nucleic acid sequences via the modifications denoted in Table 1, using conventional methods.

The G6PD protein of the invention or a biologically active section or fragments thereof may be involved in transporting energy-rich carbon-containing molecules such as glucose into *C. glutamicum* or in an intracellular signal transduction in this microorganism, or they may have one or more of the activities listed in Table 1.

The following subsections describe various aspects of the invention in more detail:

A. Isolated Nucleic Acid Molecules

One aspect of the invention relates to isolated nucleic acid molecules which encode G6PD polypeptides or biologically active sections thereof and to nucleic acid fragments which are sufficient for the use as hybridization probes or primers for identifying or amplifying G6PD-encoding nucleic acids (e.g. G6PD DNA). The term "nucleic acid molecule" is intended to comprise DNA molecules (e.g. cDNA or genomic DNA) and RNA molecules (e.g. mRNA) and also DNA or RNA analogs generated by means of nucleotide analogs. Moreover, this term comprises the untranslated sequence located at the 3' and 5' ends of the coding gene region: at least about 100 nucleotides of the sequence upstream of the 5' end of the coding region and at least about 20 nucleotides of the sequence downstream of the 3' end of the coding gene region. The nucleic acid molecule may be single-stranded or double-stranded but is preferably a double-stranded DNA. An "isolated" nucleic acid molecule is removed from other nucleic acid molecules which are present in the natural source of the nucleic acid. An "isolated" nucleic acid preferably does not have any sequences which flank the nucleic acid naturally in the genomic DNA of the organism from which the nucleic acid originates (for example sequences located at the 5' or 3' end of the nucleic acid). In various embodiments, the isolated G6PD nucleic acid molecule may have, for example, less than about 5 kb, 4 kb, 3 kb, 2 kb, 1 kb, 0.5 kb or 0.1 kb of the nucleotide sequences which naturally flank the nucleic acid molecule in the genomic DNA of the cell from which the nucleic acid originates (e.g. a *C. glutamicum* cell). In addition to this, an "isolated" nucleic acid molecule such as a cDNA molecule may be essentially free of another cellular material or culture medium, if prepared by recombinant techniques, or free of chemical precursors or other chemicals, if synthesized chemically.

A nucleic acid molecule of the invention, for example a nucleic acid molecule having a nucleotide sequence of Appendix A or a section thereof, may be prepared by means of molecular biological standard techniques and the sequence information provided here. For example, a *C. glutamicum* G6PD cDNA may be isolated from a *C. glutamicum* bank by using a complete sequence from Appendix A or a section thereof as hybridization probe and by using standard hybridization techniques (as described, for example, in Sambrook, J., Fritsch, E. F. and Maniatis, T. Molecular Cloning: A Laboratory Manual. 2nd Ed., Cold Spring Harbor Laboratory, Cold Spring Harbor Laboratory Press, Cold Spring Harbor, N.Y., 1989). Moreover, a nucleic acid molecule comprising a complete sequence from Appendix A or a section thereof can be isolated via polymerase chain reaction, using the oligonucleotide primers produced on the basis of said sequence (for example, it is possible to isolate a nucleic acid molecule comprising a complete sequence from Appendix A or a section thereof via polymerase chain reaction by using oligonucleotide primers which have been produced on the basis of this same sequence of Appendix A). For example, mRNA can be isolated from normal endothelial cells (for example via the guanidinium thiocyanate extraction method of Chirgwin et al. (1979) Biochemistry 18: 5294–5299), and the cDNA can be prepared by means of reverse transcriptase (e.g. Moloney-MLV reverse transcriptase, available from Gibco/BRL, Bethesda, Md., or AMV reverse transcriptase, available from Seikagaku America, Inc., St. Petersburg, Fla.). Synthetic oligonucleotide primers for amplification via polymerase chain reaction can be produced on the basis of any of the nucleotide sequences shown in Appendix A. A nucleic acid of the invention may be amplified by means of cDNA or, alternatively, genomic DNA as template and of suitable oligonucleotide primers according to PCR standard amplification techniques. The nucleic acid-amplified in this way may be cloned into a suitable vector and characterized by DNA sequence analysis. oligonucleotides corresponding to a G6PD nucleotide sequence may be prepared by standard syntheses using, for example, an automatic DNA synthesizer.

In a preferred embodiment, an isolated nucleic acid molecule of the invention comprises one of the nucleotide sequences listed in Appendix A.

In a further preferred embodiment, an isolated nucleic acid molecule of the invention comprises a nucleic acid molecule complementary to any of the nucleotide sequences shown in Appendix A or a section thereof, said nucleic acid molecule being sufficiently complementary to any of the nucleotide sequences shown in Appendix A for it to hybridize with any of the sequences indicated in Appendix A, resulting in a stable duplex.

In one embodiment, the nucleic acid molecule of the invention encodes a protein or a section thereof comprising an amino acid sequence which is sufficiently homologous to an amino acid sequence of Appendix B for the protein or a section thereof to be still capable of taking part in transporting energy-rich carbon molecules (such as glucose) into *C. glutamicum* and also in one or more intracellular signal transuction pathways. The term "sufficiently homologous", as used herein, relates to proteins or sections thereof whose amino acid sequences have a minimum number of identical or equivalent amino acid residues (for example an amino acid residue having a side chain similar to that of an amino acid residue in any of the sequences of Appendix B) compared to an amino acid sequence of Appendix B so that the protein or a section thereof is capable of transporting energy-rich carbon molecules such as glucose into *C. glutamicum* and, moreover, taking part in the intracellular signal transduction in this microorganism. As described herein, protein components of these metabolic pathways transport energy-rich carbon-containing molecules such as glucose into *C. glutamicum* and may also be involved in intracellular signal transduction in this microorganism. Examples of these activities are likewise described herein. Thus the "function of a G6Pb protein" relates to the complete functioning and/or to the regulation of one or more sugar transport pathways based on phosphoenolpyruvate. Table 1 lists examples of G6PD protein activities.

Sections of proteins encoded by the G6PD nucleic acid molecules of the invention are preferably biologically active sections of any of the G6PD proteins. The term "biologically active section of a G6PD protein", as used herein, is intended to comprise a section, for example a domain or a motif, of a G6PD protein, which can transport energy-rich carbon-containing molecules such as glucose into *C. glutamicum* or can be involved in intracellular signal transduction in this microorganism, or has an activity indicated in Table 1. In order to determine whether a G6PD protein or a biologically active section thereof can be involved in transporting energy-rich carbon-containing molecules such as glucose into *C. glutamicum* or in intracellular signal transduction in this microorganism, an enzyme activity assay may be carried out. These assay methods, as described in detail in example 8 of the examples, are familiar to the skilled worker.

In addition to naturally occurring variants of the G6PD sequence, which may exist in the population, the skilled worker is likewise aware of the fact that it is possible to introduce changes into a nucleotide sequence of Appendix A by mutation, leading to a change in the amino acid sequence of the encoded G6PD protein without impairing the functionality of said G6PD protein. For example, it is possible to produce in a sequence of Appendix A nucleotide substitutions which lead to amino acid substitutions at "nonessential" amino acid residues. A "nonessential" amino acid residue in a wild-type sequence of any of the G6PD proteins (Appendix B) can be modified without modifying the activity of said G6PD protein, whereas an "essential" amino acid residue is required for G6PD-protein activity. However, other amino acid residues (e.g. nonconserved or merely semiconserved amino acid residues in the domain with G6PD activity) may not be essential for said activity and thus can probably be modified without modifying said G6PD activity.

An isolated nucleic acid molecule encoding a G6PD protein which is homologous to a protein sequence of Appendix B may be generated by introducing one or more nucleotide substitutions, additions or deletions into a nucleotide sequence of Appendix A so that one or more amino acid substitutions, additions or deletions are introduced into the encoded protein. The mutations may be introduced into any of the sequences of Appendix A by standard techniques such as site-directed mutagenesis and PCR-mediated mutagenesis. Preference is given to introducing conservative amino acid substitutions at one or more of the predicted nonessential amino acid residues. A "conservative amino acid substitution" replaces the amino acid residue by an amino acid residue with a similar side chain. Families of amino acid residues with similar side chains have been defined in the art. These families comprise amino acids with basic side chains (e.g. lysine, arginine, histidine), acidic side chains (e.g. aspartic acid, glutamic acid), uncharged polar side chains (e.g. glycine, asparagine, glutamine, serine, threonine, tyrosine, cysteine), nonpolar side chains (e.g. alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine). A predicted nonessential amino acid residue in a G6PD protein is thus preferably replaced by another amino acid residue of the same side-chain family. In a further embodiment, the mutations may alternatively be introduced randomly over the entire or over part of the G6PD-encoding sequence, for example by saturation mutagenesis, and the resulting mutants may be tested for the G6PD activity described herein in order to identify mutants maintaining G6PD activity. After mutagenesis of any of the sequences of Appendix A, the encoded protein may be expressed recombinantly, and the activity of said protein may be determined, for example, using the assays described herein (see example 8 of the examples).

B. Recombinant Expression Vectors and Host Cells

A further aspect of the invention relates to vectors, preferably expression vectors, containing a nucleic acid which encodes a G6PD protein (or a section thereof). The term "vector" as used herein, relates to a nucleic acid molecule capable of transporting another nucleic acid to which it is bound. One type of vector is a "plasmid" which term means a circular double-stranded DNA loop into which additional DNA segments can be ligated. Another type of vector is a viral vector, and here additional DNA segments can be ligated into the viral genome. Certain vectors are capable of replicating autonomously in a host cell into which they have been introduced (for example bacterial vectors with bacterial origin of replication and episomal mammalian vectors). Other vectors (e.g. nonepisomal mammalian vectors) are integrated into the genome of a host cell when introduced into said host cell and thereby replicated together with the host genome. Moreover, particular vectors are capable of controlling the expression of genes to which they are functionally linked. These vectors are referred to-as "expression vectors". Normally, expression vectors used in DNA recombination techniques are in the form of plasmids.

In the present description, "plasmid" and "vector" may be used interchangeably, since the plasmid is the most commonly used type of vector. The present invention is intended to comprise said other types of expression vectors such as viral vectors (for example replication-deficient retroviruses, adenoviruses and adenovirus-related viruses), which exert similar functions.

The recombinant expression vector of the invention comprises a nucleic acid of the invention in a form which is suitable for expressing said nucleic acid in a host cell, meaning that the recombinant expression vectors comprise one or more regulatory sequences which are selected on the basis of the host cells to be used for expression and which are functionally linked to the nucleic acid sequence to be expressed. In a recombinant expression vector, the term "functionally linked" means that the nucleotide sequence of interest is bound to the regulatory sequence(s) such that expression of said nucleotide sequence is possible (for example in an in vitro transcription/translation system or in a host cell, if the vector has been introduced into said host cell). The term "regulatory sequence" is intended to comprise promoters, enhancers and other expression control elements (e.g. polyadenylation signals). These regulatory sequences are described, for example, in Goeddel: Gene Expression Technology: Methods in Enzymology 185, Academic Press, San Diego, Calif. (1990). Regulatory sequences comprise those which control constitutive expression of a nucleotide sequence in many types of host cells and those which control direct expression of the nucleotide sequence only in particular host cells. The skilled worker understands that designing an expression vector may depend on factors such as the choice of host cell to be transformed, the extent of expression of the protein of interest, etc. The expression vectors of the invention may be introduced into the host cells so as to prepare proteins or peptides, including fusion proteins or fusion peptides, which are encoded by the nucleic acids as described herein (e.g. G6PD proteins, mutant forms of G6PD proteins, fusion proteins, etc.).

The recombinant expression vectors of the invention may be designed for expressing G6PD proteins in prokaryotic or eukaryotic cells. For example, G6PD genes may be expressed in bacterial cells such as *C. glutamicum*, insect cells (using baculovirus expression vectors), yeast cells and other fungal cells (see Romanos, M. A. et al. (1992) "Foreign gene expression in yeast: a review", Yeast 8: 423–488; van den Hondel, C.A.M.J.J. et al. (1991) "Heterologous gene expression in filamentous fungi" in: More Gene Manipulations in Fungi, J. W. Bennet & L. L. Lasure, Editors, pp. 396–428: Academic Press: San Diego; and van den Hondel, C.A.M.J.J. & Punt, P. J. (1991) "Gene transfer systems and vector development for filamentous fungi in: Applied Molecular Genetics of Fungi, Peberdy, J. F. et al., Editors, pp. 1–28, Cambridge University Press: Cambridge), algal cells and multicellular plant cells (see Schmidt, R. and Willmitzer, L. (1988) "High efficiency *Agrobacterium tumefaciens*-mediated transformation of *Arabidopsis thaliana* leaf and cotyledon explants" Plant Cell Rep.: 583–586) or mammalian cells. Suitable host cells are further discussed in Goeddel, Gene Expression Technology: Methods in Enzymology 185, Academic Press, San Diego, Calif. (1990). As an alternative, the recombinant expression vector may be transcribed and translated in vitro, for example by using T7 promoter regulatory sequences and T7 polymerase.

Proteins are expressed in prokaryotes mainly by using vectors containing constitutive or inducible promoters which control expression of fusion or nonfusion proteins. Fusion vectors control a number of amino acids to a protein encoded therein, usually at the amino terminus of the recombinant protein. These fusion vectors usually have three tasks: 1) enhancing the expression of recombinant protein; 2) increasing the solubility of the recombinant protein; and 3) supporting the purification of the recombinant protein by acting as a ligand in affinity purification. Often a proteolytic cleavage site is introduced into fusion expression vectors at the junction of fusion unit and recombinant protein so that the recombinant protein can be separated from the fusion unit after purifying the fusion protein. These enzymes and their corresponding recognition sequences comprise factor Xa, thrombin and enterokinase.

Common fusion expression vectors comprise pGEX (Pharmacia Biotech Inc; Smith, D. B. and Johnson, K. S. (1988) Gene 67: 31–40), pMAL (New England Biolabs, Beverly, Mass.) und pRIT 5 (Pharmacia, Piscataway, N.J.), in which glutathione S-transferase (GST), maltose E-binding protein and protein A, respectively, are fused to the recombinant target protein. In one embodiment, the coding sequence of the G6PD protein is cloned into a pGEX expression vector such that a vector is generated, which encodes a fusion protein comprising, from N terminus to C terminus, GST—thrombin cleavage site—protein X. The fusion protein may be purified via affinity chromatography by means of a glutathione-agarose resin. The recombinant G6PD protein which is not fused to GST may be obtained by cleaving the fusion protein with thrombin.

Examples of suitable inducible nonfusion *E. coli* expression vectors include pTrc (Amann et al., (1988) Gene 69: 301–315) and pET 11d (Studier et al. Gene Expression Technology: Methods in Enzymology 185, Academic Press, San Diego, Calif. (1990) 60–89). The target gene expression from the pTrc vector is based on transcription from a hybrid trp-lac fusion promoter by host RNA polymerase. The target gene expression from the pET11d vector is based on transcription from a T7-gn10-lac fusion promoter, which is mediated by a coexpressed viral RNA polymerase (T7 gn1). This viral polymerase is provided by the BL 21 (DE3) or HMS174 (DE3) host strain by a resident λ prophage which harbors a T7 gn1 gene under the transcriptional control of the lacUV 5 promoter.

One strategy for maximizing expression of the recombinant protein is to express said protein in a host bacterium whose ability to proteolytically cleave said recombinant protein is disrupted (Gottesman, S. Gene Expression Technology: Methods in Enzymology 185, Academic Press, San Diego, Calif. (1990) 119–128). Another strategy is to modify the nucleic acid sequence of the nucleic acid to be inserted into an expression vector such that the individual codons for each amino acid are those which are preferably used in a bacterium selected for expression, such as *C. glutamicum* (Wada et al. (1992) Nucleic Acids Res. 20: 2111–2118). This modification of the nucleic acid sequences of the invention is carried out by standard techniques of DNA synthesis.

In a further embodiment, the G6PD-protein expression vector is a yeast expression vector. Examples of vectors for expression in the yeast *S. cerevisiae* include pYepSec1 (Baldari et al., (1987) Embo J. 6: 229–234), pMFa (Kurjan and Herskowitz (1982) Cell 30: 933–943), pJRY88 (Schultz et al. (1987) Gene 54: 113–123) and pYES2 (Invitrogen Corporation, San Diego, Calif.). Vectors and methods for constructing vectors which are suitable for use in other fungi such as filamentous fungi include those which are described in detail in: van den Hondel, C.A.M.J.J. & Punt, P. J. (1991) "Gene transfer systems and vector development for filamentous fungi, in: Applied Molecular Genetics of fungi, J. F. Peberdy et al., Editors, pp. 1–28, Cambridge University Press: Cambridge.

As another alternative, it is possible to express the G6PD proteins of the invention in insect cells using baculovirus expression vectors. Baculovirus vectors available for expression of proteins in cultured insect cells (e.g. Sf9 cells) include the pAc series (Smith et al., (1983) Mol. Cell Biol. 3: 2156–2165) and the pVL series (Lucklow and Summers (1989) Virology 170: 31–39).

In a further embodiment, the G6PD proteins of the invention may be expressed in unicellular plant cells (such as algae) or in cells of the higher plants (e.g. spermatophytes such as crops). Examples of expression vectors of plants include those which are described in detail in: Bekker, D., Kemper, E., Schell, J. and Masterson, R. (1992) "New plant binary vectors with selectable markers located proximal to the left border", Plant Mol. Biol. 20: 1195–1197; and Bevan, M. W. (1984) "Binary Agrobacterium vectors for plant transformation", Nucl. Acids Res. 12: 8711–8721.

A further embodiment, a nucleic acid of the invention is expressed in mammalian cells using a mammalian expression vector. Examples of mammalian expression vectors include pCDM8 (Seed, B. (1987) Nature 329:840) and pMT2PC (Kaufman et al. (1987) EMBO J. 6: 187–195). When used in mammalian cells, the control functions of the expression vector are often provided by viral regulatory elements. Commonly used promoters are derived, for example, from polyoma, adenovirus2, cytomegalovirus and simian virus 40. Other suitable expression systems for prokaryotic and eukaryotic cells can be found in chapters 16 and 17 of Sambrook, J., Fritsch, E. F. and Maniatis, T., Molecular cloning: A Laboratory Manual, 2nd Edition, Cold Spring Harbor Laboratory, Cold Spring Harbor Laboratory Press, Cold Spring Harbor, N.Y., 1989.

In a further embodiment, the recombinant mammalian expression vector may preferably cause expression of the nucleic acid in a particular cell type (for example, tissue-specific regulatory elements are used for expressing the nucleic acid). Tissue-specific regulatory elements are known in the art. Non-limiting examples of suitable tissue-specific promoters include the albumin promoter (liver-specific; Pinkert et al. (1987) Genes Dev. 1: 268–277), lymphoid-specific promoters (Calame und Eaton (1988) Adv. Immunol. 43: 235–275), in particular promoters of T-cell receptors (Winoto and Baltimore (1989) EMBO J. 8: 729–733) and immunoglobulins (Banerji et al. (1983) Cell 33: 729–740; Queen and Baltimore (1983) Cell 33: 741–748), neuron-specific promoters (e.g. neurofilament promoter; Byrne and Ruddle (1989) PNAS 86: 5473–5477), pancreas-specific promoters (Edlund et al., (1985) Science 230: 912–916) and mamma-specific promoters (e.g. milk serum promoter; U.S. Pat. No. 4,873,316 and European Patent Application document No. 264 166). Development-regulated promoters for example the murine hox promoters (Kessel and Gruss (1990) Science 249: 374–379) and the α-fetoprotein promoter (Campes and Tilghman (1989) Genes Dev. 3: 537–546), are likewise included.

Moreover, the invention provides a recombinant expression vector comprising an inventive DNA molecule which has been cloned into the expression vector in antisense direction. This means that the DNA molecule is functionally linked to a regulator sequence such that an RNA molecule which is antisense to G6PD mRNA can be expressed (via transcription of the DNA molecule). It is possible, to select regulatory sequences which are functionally bound to a nucleic acid cloned in antisense direction and which control continuous expression of the antisense RNA molecule in a multiplicity of cell types; for example, it is possible to select viral promoters and/or enhancers or regulatory sequences which control the constitutive tissue-specific or cell type-specific expression of antisense RNA. The antisense expression vector may be in the form of a recombinant plasmid, phagemid or attenuated virus and produces antisense nucleic acids under the control of a highly effective regulatory region whose activity is determined by the cell type into which the vector is introduced. The regulation of gene expression by means of antisense genes is discussed in Weintraub, H. et al., Antisense-RNA as a molecular tool for genetic analysis, Reviews—Trends in Genetics, Vol. 1(1) 1986.

A further aspect of the invention relates to the host cells into which a recombinant expression vector of the invention has been introduced. The terms "host cell" and "recombinant host cell" are used interchangeably herein. Naturally, these terms relate not only to a particular target cell but also to the progeny or potential progeny of this cell. Since particular modifications may appear in successive generations, due to mutation or environmental factors, this progeny is not necessarily identical to the parental cell but is still included within the scope of the term as used herein.

A host cell may be a prokaryotic or eukaryotic cell. For example, a G6PD protein may be expressed in bacterial cells such as *C. glutamicum*, insect cells, yeast cells or mammalian cells (such as Chinese hamster ovary (CHO) cells or COS cells). Other suitable host cells are familiar to the skilled worker. Microorganisms which are related to *Corynebacterium glutamicum* and can be used in a suitable manner as host cells for the nucleic acid and protein molecules of the invention are listed in Table 3.

Conventional transformation or transfection methods can be used to introduce vector DNA into prokaryotic or eukaryotic cells. The terms "transformation" and "transfection", as used herein, are intended to comprise a multiplicity of methods known in the art for introducing foreign nucleic acid (e.g. DNA) into a host cell, including calcium phosphate or calcium chloride coprecipitation, DEAE dextran-mediated transfection, lipofection or electroporation. Suitable methods for transformation or transfection of host cells can be found in Sambrook et al. (Molecular Cloning: A Laboratory Manual. 2nd Edition, Cold Spring Harbor Laboratory, Cold Spring Harbor Laboratory Press, Cold Spring Harbor, N.Y., 1989) and other laboratory manuals.

In the case of stable transfection of mammalian cells, it is known that, depending on the expression vector used and transfection technique used, only a small proportion of the cells integrate the foreign DNA into their genome. These integrants are usually identified and selected by introducing a gene which encodes a selectable marker (e.g. resistant to antibiotics) together with the gene of interest into the host cells. Preferred selectable markers include those which impart resistance to drugs such as G418, hygromycin and methotrexate. A nucleic acid which encodes a selectable marker may be introduced into a host cell on the same vector that encodes a G6PD protein or may be introduced in a separate vector. Cells which have been stably transfected with the introduced nucleic acid may be identified by drug selection (for example, cells which have integrated the selectable marker survive, whereas the other cells die).

A homologous recombined microorganism is generated by preparing a vector which contains at least one G6PD-gene section into which a deletion, addition or substitution has been introduced in order to modify, for example functionally disrupt, the G6PD gene. Said G6PD gene is preferably a *Corynebacterium glutamicum* G6PD gene, but it is also possible to use a homolog from a related bacterium or even from a mammalian, yeast or insect source. In a preferred embodiment, the vector is designed such that homologous recombination functionally disrupts the endogenous G6PD gene (i.e., the gene no longer encodes a functional protein; likewise referred to as "knockout" vector). As an alternative, the vector may be designed such that homologous recombination mutates or otherwise modifies the endogenous G6PD gene which, however, still encodes the functional protein (for example, the regulatory region located upstream may be modified such that thereby expression of the endogenous G6PD protein is modified.). The modified G6PD-gene fraction in the homologous recombination vector is flanked at its 5' and 3' ends by additional nucleic acids of the G6PD gene, which makes possible a homologous recombination between the exogenous G6PD gene carried by the vector and an endogenous G6PD gene in a microorganism. The length of the additional flanking G6PD nucleic acid is sufficient for a successful homologous recombination with the endogenous gene. Usually, the vector contains several kilobases of flanking DNA (both at the 5' and the 3' ends) (see, for example, Thomas, K. R. and Capecchi, M. R. (1987) Cell 51: 503, for a description of homologous recombination vectors). The vector is introduced into a microorganism (e.g. by electroporation) and cells in which the introduced G6PD gene has homologously recombined with the endogenous G6PD gene are selected using methods known in the art.

In another embodiment, it is possible to produce recombinant microorganisms which contain selected systems which make possible a regulated expression of the introduced gene. The insertion of a G6PD gene under the control of the lac operon in a vector enables, for example, G6PD-gene expression only in the presence of IPTG. These regulatory systems are known in the art.

A host cell of the invention, such as a prokaryotic or eukaryotic host cell in culture, may be used for producing (i.e. expressing) a G6PD protein. Moreover, the invention provides methods for producing G6PD proteins by using the host cells of the invention. In one embodiment, the method comprises the cultivation of the host cell of the invention (into which a recombinant expression vector encoding a G6PD protein has been introduced or in whose genome a gene encoding a wild-type or modified G6PD protein has been introduced) in a suitable medium until the G6PD protein has been produced. In a further embodiment, the method comprises isolating the G6PD proteins from the medium or the host cell.

C. Uses and Methods of the Invention

The nucleic acid molecules, proteins, protein homologs, fusion proteins, primers, vectors and host cells described herein may be used in one or more of the following methods: identification of *C. glutamicum* and related organisms, mapping of genomes of organisms related to *C. glutamicum*, identification and localization of *C. glutamicum* sequences of interest, evolutionary studies, determination of G6PD-protein regions required for function, modulation of the activity of G6PD protein; modulation of the activity of a G6PD pathway; and modulation of the cellular production of a compound of interest, such as a fine chemical. The G6PD nucleic acid molecules of the invention have a multiplicity of uses. First, they may be used for identifying an organism as *Corynebacterium glutamicum* or close relatives thereof. They may also be used for identifying *C. glutamicum* or a relative thereof in a mixed population of microorganisms.

The invention provides the nucleic acid sequences of a number of *C. glutamicum* genes. Probing the extracted genomic DNA of a culture of a uniform or mixed population of microorganisms under stringent conditions with a probe which comprises a region of a *C. glutamicum* gene which is unique for this organism makes it possible to determine whether said organism is present. Although *Corynebacterium glutamicum* itself is nonpathogenic, it is related to pathogenic species such as *Corynebacterium diphtheriae*. The detection of such an organism is of substantial clinical importance.

The nucleic acid and protein molecules of the invention may serve as markers for specific regions of the genome. This is useful not only for mapping the genome but also for functional studies of *C. glutamicum* proteins. The genomic region to which a particular *C. glutamicum* DNA-binding protein binds may be identified, for example, by cleaving the *C. glutamicum* genome and incubating the fragments with the DNA-binding protein. Those fragments which bind the protein may additionally be probed with the nucleic acid molecules of the invention, preferably by using ready detectable labels; binding of such a nucleic acid molecule to the genomic fragment makes it possible to locate the fragment on the map of the *C. glutamicum* genome, and, when carrying out the process several times using different enzymes, facilitates rapid determination of the nucleic acid sequence to which the protein binds. Moreover, the nucleic acid molecules of the invention may be sufficiently homologous to the sequences of related species for these nucleic acid molecules to serve as markers for constructing a genomic map in related bacteria such as *Brevibacterium lactofermentum*.

The G6PD nucleic acid molecules of the invention are likewise suitable for evolutionary studies and protein structure studies. The system for taking up sugars, in which the molecules of the invention are involved, is utilized by many bacteria; comparison of the sequences of the nucleic acid molecules of the invention with those encoding similar enzymes of other organisms makes it possible to determine the degree of evolutionary relationship of said organisms. Correspondingly, such a comparison makes it possible to determine which sequence regions are conserved and which are not, and this can be helpful in determining those regions of the protein, which are essential for enzyme function. This type of determination is valuable for protein engineering studies and may give an indication as to which protein can tolerate mutagenesis without losing its function.

Manipulation of the G6PD nucleic acid molecules of the invention may cause the production of G6PD proteins with functional differences to wild-type G6PD proteins. These proteins may be improved with respect to their efficiency or activity, may be present in the cell in larger amounts than normal or may be weakened with respect to their efficiency or activity.

The G6PD molecules of the invention may be modified in such a way that the yield, production and/or efficiency of production of one or more fine chemicals is improved. It is possible, by modifying a G6PD protein involved in taking up glucose for it to have optimal activity, to increase the extent of glucose uptake or the rate at which glucose is transported into the cell. The degradation of glucose and other sugars inside the cell provides the energy which may be used for driving energetically unfavorable biochemical reactions such as those involved in the biosynthesis of fine chemicals. Said degradation likewise provides intermediates and precursors for the biosynthesis of particular fine chemicals such as amino acids, vitamins and cofactors. It is therefore possible, by increasing the amount of intracellular energy-rich carbon molecules via modification of the G6PD molecules of the invention, to increase the energy available for carrying out metabolic pathways which are required for producing one or more fine chemicals and also the intracellular pools of metabolites required for said production. Conversely, it is possible, by lowering the import of a sugar whose degradation products include a compound which is used only in metabolic pathways competing for enzymes, cofactors or intermediates with metabolic pathways for producing a fine chemical of interest, to downregulate said metabolic pathway and thus perhaps increase production by the biosynthetic pathway of interest.

The G6PD molecules of the invention may be involved in one or more intracellular signal transduction pathways which influence the yields and/or rate of production of one or more fine chemicals from *C. glutamicum*. For example, proteins required for importing one or more sugars from the extracellular medium (e.g. HPr, enzyme I or a component of an enzyme II complex) are, in the presence of a sufficient amount of said sugar in the cell, frequently posttranslationally modified so that they are no longer capable of importing said sugar. An example of this takes place in *E. coli* in which high intracellular fructose 1,6-bisphosphate levels cause phosphorylation of HPr at serine 46, after which said molecule can no longer take part in transporting a sugar. Although this intracellular sugar level at which the transport system is switched off may be sufficient in order to maintain normal cellular function, it limits overproduction of the fine chemical of interest. It is therefore desirable to modify the G6PD proteins of the invention such that they are no longer susceptible to such a negative regulation. As a result, higher intracellular concentrations of one or more sugars and, by extension, a more efficient production or higher yields of one or more fine chemicals from organisms containing these mutant G6PD proteins are attained.

This abovementioned list of strategies for the mutagenesis of G6PD proteins, which ought to increase the yields of a compound of interest, is not intended to be limiting; variations of these mutagenesis strategies are quite obvious to the skilled worker. These mechanisms make it possible to use the nucleic acid and protein molecules of the invention in order to generate *C. glutamicum* or related bacterial strains expressing mutated G6PD nucleic acids and protein molecules so as to improve the yield, production and/or efficiency of production of a compound of interest. The compound of interest may be a *C. glutamicum* product which comprises the end products of the biosynthetic pathways and intermediates of naturally occurring metabolic pathways and also molecules which do not naturally occur in the *C. glutamicum* metabolism but are produced by a *C. glutamicum* strain of the invention.

The following examples which are not to be understood as being limiting further illustrate the present invention. The contents of all references, patent applications, patents and published patent applications cited in this patent application are hereby incorporated by way of reference.

EXAMPLES

Example 1

Preparation of Total Genomic DNA from *Corynebacterium glutamicum* ATCC13032

A *Corynebacterium glutamicum* (ATCC 13032) culture was cultivated with vigorous shaking in BHI medium (Difco) at 30° C. overnight. The cells were harvested by centrifugation, the supernatant was discarded and the cells were resuspended in 5 ml of buffer I (5% of the original culture volume—all volumes stated have been calculated for a culture volume of 100 ml). Composition of buffer I: 140.34 g/l sucrose, 2.46 g/l $MgSO_4.7\ H_2O$, 10 ml/l $KH_2PO_4$ solution (100 g/l, adjusted to pH 6.7 with KOH), 50 ml/l M12 concentrate (10 g/l $(NH_4)_2SO_4$, 1 g/l NaCl, 2 g/l $MgSO_4.7\ H_2O$, 0.2 g/l $CaCl_2$, 0.5 g/l yeast extract (Difco), 10 ml/l trace element mixture (200 mg/l $FeSO_4.\ H_2O$, 10 mg/l $ZnSO_4.7\ H_2O$, 3 mg/l $MnCl_2.4\ H_2O$, 30 mg/l $H_3BO_3$, 20 mg/l $CoCl_2.6\ H_2O$, 1 mg/l $NiCl_2.6\ H_2O$, 3 mg/l $Na_2MoO_4.2\ H_2O$, 500 mg/l complexing agents (EDTA or citric acid), 100 ml/l vitamin mixture (0.2 ml/l biotin, 0.2 mg/l folic acid, 20 mg/l p-aminobenzoic acid, 20 mg/l riboflavin, 40 mg/l Ca panthothenate, 140 mg/l nicotinic acid, 40 mg/l pyridoxol hydrochloride, 200 mg/l myoinositol). Lysozyme was added to the suspension at a final concentration of 2.5 mg/ml. After incubation at 37° C. for approx. 4 h, the cell wall was degraded and the protoplasts obtained were harvested by centrifugation. The pellet was washed once with 5 ml of buffer I and once with 5 ml of TE buffer (10 mM Tris-HCl, 1 mM EDTA, pH 8). The pellet was resuspended in 4 ml of TE buffer and 0.5 ml of SDS solution (10%) and 0.5 ml of NaCl solution (5 M) were added. After addition of proteinase K at a final concentration of 200 μg/ml, the suspension was incubated at 37° C. for approx. 18 h. The DNA was purified via extraction with phenol, phenol/chloroform/isoamyl alcohol and chloroform/isoamyl alcohol by means of standard methods. The DNA was then precipitated by addition of 1/50 volume of 3 M sodium acetate and 2 volumes of ethanol, subsequent incubation at −20° C. for 30 min and centrifugation at 12 000 rpm in a high-speed centrifuge using an SS34 rotor (Sorvall) for 30 min. The DNA was dissolved in 1 ml of TE buffer containing 20 μg/ml RNase A and dialyzed against 1000 ml of TE buffer at 4° C. for at least 3 h. The buffer was exchanged 3 times during this period. 0.4 ml of 2 M LiCl and 0.8 ml of ethanol were added to 0.4 ml aliquots of the dialyzed DNA solution. After incubation at −20° C. for 30 min, the DNA was collected by centrifugation (13 000 rpm, Biofuge Fresco, Heraeus, Hanau, Germany). The DNA pellet was dissolved in TE buffer. It was possible to use DNA prepared by this method for all purposes, including Southern blotting and constructing genomic libraries.

Example 2

Construction of Genomic *Corynebacterium glutamicum* (ATCC13032) Banks in *Escherichia coli*

Starting from DNA prepared as described in Example 1, cosmid and plasmid banks were prepared according to known and well-established methods (see, for example, Sambrook, J. et al. (1989) "Molecular Cloning: A Laboratory Manual". Cold Spring Harbor Laboratory Press or Ausubel, F. M. et al. (1994) "Current Protocols in Molecular Biology", John Wiley & Sons).

It was possible to use any plasmid or cosmid. Particular preference was given to using the plasmids pBR322 (Sutcliffe, J. G. (1979) Proc. Natl Acad. Sci. USA, 75: 3737–3741); pACYC177 (Change & Cohen (1978) J. Bacteriol. 134: 1141–1156); pBS series plasmids (pBSSK+, pBSSK− and others; Stratagene, LaJolla, USA) or cosmids such as SuperCos1 (Stratagene, LaJolla, USA) or Lorist6 (Gibson, T. J. Rosenthal, A., and Waterson, R. H. (1987) Gene 53: 283–286.

Example 3

DNA Sequencing and Functional Computer Analysis

Genomic banks, as described in Example 2, were used for DNA sequencing according to standard methods, in particular the chain termination method using ABI377 sequencers (see, for example, Fleischman, R. D. et al. (1995) "Whole-genome Random Sequencing and Assembly of Haemophilus Influenzae Rd., Science 269; 496–512). Sequencing primers having the following nucleotide sequences were used: 5'-GGAAACAGTATGACCATG-3' oder 5'-GTAAAAC-GACGGCCAGT-3'.

Example 4

In Vivo Mutagenesis

In vivo mutagenesis of Corynebacterium glutamicum may be carried out by passing a plasmid (or other vector) DNA through E. coli or other microorganisms (e.g. Bacillus spp. or yeasts such as Saccharomyces cerevisiae) which cannot maintain the integrity of their genetic information. Common mutator strains contain mutations in the genes for the DNA repair system (e.g., mutHLS, mutD, mutT, etc., for comparison see Rupp, W. D. (1996) DNA repair mechanisms in Escherichia coli and Salmonella, pp. 2277–2294, ASM: Washington). These strains are known to the skilled worker. The use of these strains is illustrated, for example, in Greener, A. and Callahan, M. (1994) Strategies 7; 32–34.

Example 5

DNA Transfer between Escherichia coli and Corynebacterium glutamicum

A plurality of Corynebacterium and Brevibacterium species contain endogenous plasmids (such as, for example, pHM1519 or pBL1) which replicate autonomously (for a review see, for example, Martin, J. F. et al. (1987) Biotechnology 5: 137–146). Shuttle vectors for Escherichia coli and Corynebacterium glutamicum can be constructed readily by means of standard vectors for E. coli (Sambrook, J. et al., (1989), "Molecular Cloning: A Laboratory Manual", Cold Spring Harbor Laboratory Press or Ausubel, F. M. et al. (1994) "Current Protocols in Molecular Biology", John Wiley & Sons), to which an origin of replication for and a suitable marker from Corynebacterium glutamicum is added. Such origins of replication are preferably taken from endogenous plasmids which have been isolated from Corynebacterium and Brevibacterium species. Particular use as transformation markers for these species are genes for kanamycin resistance (such as those derived from the Tn5 or the Tn903 transposon) or for chloramphenicol (Winnacker, E. L. (1987) "From Genes to Clones—Introduction to Gene Technology, VCH, Weinheim). There are numerous examples in the literature for preparing a large multiplicity of shuttle vectors which are replicated in E. coli and C. glutamicum and which can be used for various purposes, including the overexpression of genes (see, for example, Yoshihama, M. et al. (1985) J. Bacteriol. 162: 591–597, Martin, J. F. et al., (1987) Biotechnology, 5: 137–146 and Eikmanns, B. J. et al. (1992) Gene 102: 93–98).

Standard methods make it possible to clone a gene of interest into one of the above-described shuttle vectors and to introduce such hybrid vectors into Corynebacterium glutamicum strains. C. glutamicum can be transformed via protoplast transformation (Kastsumata, R. et al., (1984) J. Bacteriol. 159, 306–311), electroporation (Liebl, E. et al., (1989) FEMS Microbiol. Letters, 53: 399–303) and, in cases in which specific vectors are used, also via conjugation (as described, for example, in Schäfer, A., et al. (1990) J. Bacteriol. 172: 1663–1666). Likewise, it is possible to transfer the shuttle vectors for C. glutamicum to E. coli by preparing plasmid DNA from C. glutamicum (by means of standard methods known in the art) and transforming it into E. coli. This transformation step can be carried out using standard methods but advantageously an Mcr-deficient E. coli strain such as NM522 (Gough & Murray (1983) J. Mol. Biol. 166: 1–19) is used.

Example 6

Determination of the Expression of the Mutated Protein

The observations of the activity of a mutated protein in a transformed host cell are based on the fact that the mutated protein is expressed in a similar manner and in similar quantity to the wild-type protein. A suitable method for determining the amount of transcription of the mutated gene (an indication of the amount of mRNA available for translation of the gene product) is to carry out a Northern blot (see, for example, Ausubel et al., (1988) Current Protocols in Molecular Biology, Wiley: N.Y.), with a primer which is designed such that it binds to the gene of interest being provided with a detectable (usually radioactive or chemiluminescent) label such that—when the total RNA of a culture of the organism is extracted, fractionated on a gel, transferred to a stable matrix and incubated with this probe—binding and binding quantity of the probe indicate the presence and also the amount of mRNA for said gene. This information is an indicator of the extent to which the mutant gene has been transcribed. Total cell RNA can be isolated from Corynebacterium glutamicum by various methods known in the art, as described in Bormann, E. R. et al., (1992) Mol. Microbiol. 6: 317–326.

The presence or the relative amount of protein translated from said mRNA can be determined by using standard techniques such as Western blot (see, for example, Ausubel et al. (1988) "Current Protocols in Molecular Biology", Wiley, N.Y.). In this method, total cell proteins are extracted, separated by gel electrophoresis, transferred to a matrix such as nitrocellulose and incubated with a probe, for example an antibody, which binds specifically to the protein of interest. This probe is usually provided with a chemiluminescent or colorimetric label which can be readily detected. The presence and the observed amount of label indicate the presence and the amount of the desired mutant protein in the cell.

Example 7

Growth of Genetically Modified Corynebacterium Glutamicum—Media and Cultivation Conditions Genetically modified corynebacteria are cultivated in synthetic or natural growth media. A number of different growth media for corynebacteria are known and readily available (Lieb et al. (1989) Appl. Microbiol. Biotechnol. 32: 205–210; von der Osten et al. (1998) Biotechnology Letters 11: 11–16; Patent DE 4 120 867; Liebl (1992) "The Genus *Corynebacterium*", in: The Procaryotes, Vol. II, Balows, A., et al., editors Springer-Verlag). These media are composed of one or more carbon sources, nitrogen sources, inorganic salts, vitamins and trace elements. Preferred carbon sources are sugars such as mono-, di- or polysaccharides. Examples of very good carbon sources are glucose, fructose, mannose, galactose, ribose, sorbose, ribulose, lactose, maltose, sucrose, raffinose, starch and cellulose. Sugars may also be added to the media via complex compounds such as molasses or other byproducts from sugar refining. It may also be advantageous to add mixtures of various carbon sources. Other possible carbon sources are alcohols and organic acids, such as methanol, ethanol, acetic acid or lactic acid. Nitrogen sources are usually organic or inorganic nitrogen compounds or materials containing these compounds. Examples of nitrogen sources include ammonia gas and ammonium salts such as $NH_4Cl$ or $(NH_4)_2SO_4$, $NH_4OH$, nitrates, urea, amino acids and complex nitrogen sources such as cornsteep liquor, soya meal, soya protein, yeast extracts, meat extracts and others.

Inorganic salt compounds which may be present in the media include the chloride, phosphorus or sulfate salts of calcium, magnesium, sodium, cobalt, molybdenum, potassium, manganese, zinc, copper and iron. Chelating agents may be added to the medium in order to keep the metal ions in solution. Particularly suitable chelating agents include dihydroxyphenols such as catechol or protocatechuate and organic acids such as citric acid. The media usually also contain other growth factors such as vitamins or growth promoters, examples of which include biotin, riboflavin, thiamine, folic acid, nicotinic acid, panthothenate and pyridoxine. Growth factors and salts are frequently derived from complex media components such as yeast extract, molasses, cornsteep liquor and the like. The exact composition of the media heavily depends on the particular experiment and is decided upon individually for each case. Information on the optimization of media can be found in the textbook "Applied Microbiol. Physiology, A Practical Approach" (editors P. M. Rhodes, P. F. Stanbury, IRL Press (1997) pp. 53–73, ISBN 0 19 963577 3). Growth media can also be obtained from commercial suppliers, for example Standard 1 (Merck) or BHI (brain heart infusion, DIFCO) and the like.

All media components are sterilized, either by heat (20 min at 1.5 bar and 121° C.) or by sterile filtration. The components may be sterilized either together or, if required, separately. All media components may be present at the start of the cultivation or added continuously or batchwise, as desired.

The cultivation conditions are defined separately for each experiment. The temperature should be between 15° C. and 45° C. and may be kept constant or may be altered during the experiment. The pH of the medium should be in the range from 5 to 8.5, preferably around 7.0 and may be maintained by adding buffers to the media. An example of a buffer for this purpose is a potassium phosphate buffer. Synthetic buffers such as MOPS, HEPES; ACES, etc. may be used alternatively or simultaneously. Addition of NaOH or $NH_4OH$ can also keep the pH constant during cultivation. If complex media components such as yeast extract are used, the demand for additional buffers decreases, since many complex compounds have a high buffer capacity. In the case of using a fermenter for cultivating microorganisms, the pH may also be regulated using gaseous ammonia.

The incubation period is usually in a range from several hours to several days. This time is selected such that the maximum amount of product accumulates in the broth. The growth experiments disclosed may be carried out in a multiplicity of containers such as microtiter plates, glass tubes, glass flasks or glass or metal fermenters of different sizes. For the screening of a large number of clones, the microorganisms should be grown in microtiter plates, glass tubes or shaker flasks either with or without baffles. Preference is given to using 100 ml shaker flasks which are filled with 10% (based on volume) of the required growth medium. The flasks should be shaken on an orbital shaker (amplitude 25 mm) at a speed in the range of 100–300 rpm. Losses due to evaporation can be reduced by maintaining a humid atmosphere; alternatively, the losses due to evaporation should be corrected mathematically.

If genetically modified clones are investigated, an unmodified control clone or a control clone containing the basic plasmid without insert should also be assayed. The medium is inoculated to an $OD_{600}$ of 0.5–1.5, with cells being used which have been grown on agar plates such as CM plates (10 g/l glucose, 2.5 g/l NaCl, 2 g/l urea, 10 g/l polypeptone, 5 g/l yeast extract, 5 g/l meat extract, 22 g/l agar pH 6.8 with 2 M NaOH) which have been incubated at 30° C. The media are inoculated either by introducing a saline solution of *C. glutamicum* cells from CM plates or by adding a liquid preculture of said bacterium.

Example 8

In vitro Analysis of the Function of Mutated Proteins

The determination of the activities and kinetic parameters of enzymes is well known in the art. Experiments for determining the activity of a particular modified enzyme must be adapted to the specific activity of the wild-type enzyme, and this is within the capabilities of the skilled worker. Overviews regarding enzymes in general and also specific details concerning the structure, kinetics, principles, methods, applications and examples of the determination of many enzyme activities can be found, for example, in the following references: Dixon, M., and Webb, E. C: (1979) Enzymes, Longmans, London; Fersht (1985) Enzyme Structure and Mechanism, Freeman, New York; Walsh (1979) Enzymatic Reaction Mechanisms. Freeman, San Francisco; Price, N.C., Stevens, L. (1982) Fundamentals of Enzymology. Oxford Univ. Press: Oxford; Boyer, P. D: editors (1983) The Enzymes, 3rd edition, Academic Press, New York; Bisswanger, H. (1994) Enzymkinetik, 2nd edition VCH, Weinheim (ISBN 3527300325); Bergmeyer, H. U., Bergmeyer, J., Graβ1, M. editors (1983–1986) Methods of Enzymatic Analysis, 3rd edition, Vol. I–XII, Verlag Chemie: Weinheim; and Ullmann's Encyclopedia of Industrial Chemistry (1987) Vol. A9, "Enzymes", VCH, Weinheim, pp. 352–363.

The activity of proteins binding to DNA can be measured by many well-established methods such as DNA bandshift assays (which are also referred to as gel retardation assays). The action of these proteins on the expression of other molecules can be measured using reporter gene assays (as described in Kolmar, H. et al., (1995) EMBO J. 14: 3895–3904 and in references therein). Reporter gene assay systems are well known and established for applications in prokaryotic and eukaryotic cells, with enzymes such as beta-galactosidase, green fluorescent protein and several other enzymes being used.

The activity of membrane transport proteins can be determined according to the techniques described in Gennis, R. B. (1989) "Pores, Channels and Transporters", in Biomembranes, Molecular Structure and Function, Springer: Heidelberg, pp. 85–137; 199–234; and 270–322.

Example 9

Analysis of the Influence of Mutated Protein on the Production of the Product of Interest The effect of the genetic modification in *C. glutamicum* on the production of a compound of interest (such as an amino acid) can be determined by growing the modified microorganisms under suitable conditions (such as those described above) and testing the medium and/or the cellular components for increased production of the product of interest (i.e. an amino acid). Such analytical techniques are well known to the skilled worker and include spectroscopy, thin-layer chromatography, various types of coloring methods, enzymic and microbiological methods and analytical chromatography such as high performance liquid chromatography (see, for example, Ullman, Encyclopedia of Industrial Chemistry, Vol. A2, pp. 89–90 and pp. 443–613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469–714, VCH: Weinheim; Belter, P. A. et al. (1988) Bioseparations: downstream processing for Biotechnology, John Wiley and Sons; Kennedy, J. F. and Cabral, J. M. S. (1992) Recovery processes for biological Materials, John Wiley and Sons; Shaeiwitz, J. A. and Henry, J. D. (1988) Biochemical Separations, in Ullmann's Encyclopedia of Industrial Chemistry, Vol. B3; Chapter 11, pp. 1–27, VCH: Weinheim; and Dechow, F. J. (1989) Separation and purification techniques in biotechnology, Noyes Publications).

In addition to measuring the end product of the fermentation, it is likewise possible to analyze other components of the metabolic pathways, which are used for producing the compound of interest, such as intermediates and byproducts, in order to determine the overall productivity of the organism, the yield and/or the efficiency of production of the compound. The analytical methods include measuring the amounts of nutrients in the medium (for example sugars, hydrocarbons, nitrogen sources, phosphate and other ions), measuring biomass composition and growth, analyzing the production of common metabolites from biosynthetic pathways and measuring gases generated during fermentation. Standard methods for these measurements are described in Applied Microbial Physiology; A Practical Approach, P. M. Rhodes and P. F. Stanbury, editors IRL Press, pp. 103–129; 131–163 and 165–192 (ISBN: 0199635773) and the references therein.

Example 10

Purification of the Product of Interest from a *C. glutamicum* Culture

The product of interest may be obtained from *C. glutamicum* cells or from the supernatant of the above-described culture by various methods known in the art. If the product of interest is not secreted by the cells, the cells may be harvested from the culture by slow centrifugation, and the cells may be lysed by standard techniques such as mechanial force or sonication. The cell debris is removed by centrifugation and the supernatant fraction which contains the soluble proteins is obtained for further purification of the compound of interest. If the product is secreted by the *C. glutamicum* cells, the cells are removed from the culture by slow centrifugation and the supernatant fraction is retained for further purification.

The supernatant fraction from both purification methods is subjected to chromatography using a suitable resin, and either the molecule of interest is retained on the chromatography resin while many contaminants in the sample are not, or the contaminants remain on the resin while the sample does not. If necessary, these chromatography steps can be repeated using the same or different chromatography resins. The skilled worker is familiar with the selection of suitable chromatography resins and the most effective application for a particular molecule to be purified. The purified product may be concentrated by filtration or ultrafiltration and stored at a temperature at which product stability is highest.

In the art, many purification methods are known which are not limited to the above purification method and which are described, for example, in Bailey, J. E. & Ollis, D. F. Biochemical Engineering Fundamentals, McGraw-Hill: New York (1986).

The identity and purity of the isolated compounds can be determined by standard techniques of the art. These techniques comprise high performance liquid chromatography (HPLC), spectroscopic methods, coloring methods, thin-layer chromatography, NIRS, enzyme assays or microbiological assays. These analytical methods are compiled in: Patek et al. (1994) Appl. Environ. Microbiol. 60: 133–140; Malakhova et al. (1996) Biotekhnologiya 11: 27–32; and Schmidt et al. (1998) Bioprocess Engineer. 19: 67–70. Ulmann's Encyclopedia of Industrial Chemistry (1996) Vol. A27, VCH: Weinheim, pp. 89–90, pp. 521–540, pp. 540–547, pp. 559–566, 575–581 and pp. 581–587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Vol. 17.

EQUIVALENTS

The skilled worker knows, or can identify by using simply routine methods, a large number of equivalents of the specific embodiments of the invention. These equivalents are intended to be included in the patent claims below.

The information in Table 1 is to be understood as follows:

In column 1, "DNA ID", the relevant number refers in each case to the SEQ ID NO of the enclosed sequence listing. Consequently, "5" in column "DNA ID" is a reference to SEQ ID NO:5.

In column 2, "AA ID", the relevant number refers in each case to the SEQ ID NO of the enclosed sequence listing. Consequently, "6" in column "AA ID" is a reference to SEQ ID NO:6.

In column 3, "Identification", an unambiguous internal name for each sequence is listed.

In column 4, "AA post", the relevant number refers in each case to the amino acid position of the polypeptide sequence "AA ID" in the same row. Consequently, "26" in column "AA pos" is amino acid position 26 of the polypeptide sequence indicated accordingly. Position counting starts at the N terminus with +1.

In column 5, "AA wild type", the relevant letter refers in each case to the amino acid, displayed in the one-letter code, at the position in the corresponding wild-type strain, which is indicated in column 4.

In column 6, "AA mutant", the relevant letter refers in each case to the amino acid, displayed in the one-letter code, at the position in the corresponding mutant strain, which is indicated in column 4.

In column 7, "Function", the physiological function of the corresponding polypeptide sequence is listed.

One-letter code of the proteinogenic amino acids:
A Alanine
C Cysteine
D Aspartic acid
E Glutamic acid
F Phenylalanine
G Glycine
H His
I Isoleucine
K Lysine
L Leucine
M Methionine
N Asparagine
P Proline
Q Glutamine
R Arginine
S Serine
T Threonine
V Valine
W Tryptophan
Y Tyrosine

TABLE 1

Gene coding for glucose-6-phosphate-dehydrogenase proteins

| DNA ID: | AA ID: | Identification: | AA pos: | AA wild type | AA mutant | Function: |
|---|---|---|---|---|---|---|
| 1 | 2 | RXA02737 | 243 | A | T | Glucose-6-phosphate dehydrogenase |

---

We claim:

1. An isolated nucleic acid molecule, or the complement thereof, encoding the amino acid sequence set forth in SEQ ID NO: 2, wherein the amino acids residue at position 243 of SEQ ID NO: 2 is any amino acid except for alanine.

2. An isolated nucleic acid molecule, or the complement thereof, comprising the nucleotide sequence set forth in SEQ ID NO:1, wherein the nucleic acid molecule comprises one or more nucleic acid modifications at nucleotide residues 827–829 of SEQ ID NO:1 such that nucleotide residues 827–829 of SEQ ID NO:1 encode any amino acid except alanine.

3. The isolated nucleic acid molecule of claim 1, wherein the amino acid residue at position 243 of SEQ ID NO:2 is threonine.

4. A vector comprising the nucleic acid molecule of claim 1 or 2.

5. The vector of claim 4, which is an expression vector.

6. An isolated host cell comprising the vector of claim 5.

7. The host cell of claim 6, wherein said host cell is a bacterial host cell capable of producing an amino acid and wherein expression of said amino acid molecule modulates the production of the amino acid from said bacterial cell.

8. A method for preparing an amino acid comprising culturing the host cell of claim 6, wherein said host cell is a bacterial host cell capable of producing the amino acid, such that the amino acid is produced.

9. The method of claim 8, wherein said amino acid is lysine.

10. The nucleic acid molecule of claim 2, wherein nucleotide residues 827–829 of SEQ ID NO:1 encode threonine.

11. The host cell of claim 6, wherein said cell belongs to the bacterial genus *Corynebacterium* or *Brevibacterium*.

12. The method of claim 8, wherein expression of the nucleic acid molecule from said vector results in modulation of production of said amino acid.

13. A method for producing an amino acid, comprising culturing a bacterial cell capable of producing the amino acid, wherein the genomic DNA of the cell has been altered by the inclusion of a nucleic acid molecule of claim 1 or 2.

14. The method of claim 8, wherein said amino acid is glutamic acid.

* * * * *